United States Patent [19]

Dornheim

[11] 4,365,344
[45] Dec. 21, 1982

[54] STAND FOR AN X-RAY IMAGE DETECTION APPARATUS WHICH IS INSERTABLE BENEATH THE PATIENT SUPPORT OF AN X-RAY EXAMINATION APPARATUS

[75] Inventor: Hans-Peter Dornheim, Bubenreuth, Fed. Rep. of Germany

[73] Assignee: Siemens Aktiengesellschaft, Berlin & Munich, Fed. Rep. of Germany

[21] Appl. No.: 225,311

[22] Filed: Jan. 15, 1981

[30] Foreign Application Priority Data

Feb. 4, 1980 [DE] Fed. Rep. of Germany ....... 3003976

[51] Int. Cl.³ .............................................. G03B 41/16
[52] U.S. Cl. ..................................... 378/189; 378/209
[58] Field of Search ........................ 250/521, 468, 444; 378/189, 190, 177, 181

[56] References Cited

U.S. PATENT DOCUMENTS 3,434,684 3/1969 Warden ................................ 250/521
4,233,516 11/1980 Trepte ................................. 250/521

FOREIGN PATENT DOCUMENTS 689324 3/1953 United Kingdom ................ 250/521

Primary Examiner—Craig E. Church
Attorney, Agent, or Firm—Hill, Van Santen, Steadman, Chiara & Simpson

[57] ABSTRACT

In an exemplary embodiment in order to obstruct the examination of the patient as little as possible and simultaneously render possible a rapid shift of the working position of the image detection apparatus from a horizontal position immediately beneath the patient support platform to a vertical position immediately above the patient support platform, the disclosure provides that the lifting carriage exhibits an essentially angled configuration and that the image detection apparatus is pivotally mounted on the free end of the horizontal leg of the lifting carriage, that the stand carriage, the lifting carriage (guided on the stand carriage) and the support-mounting (pivotally mounted on the lifting carriage) are arranged beneath the image detection apparatus, and that coupling elements (which are capable of being brought into engagement with the x-ray examination apparatus) are connected with the stand carriage. Moreover, the guidance of the lifting carriage on the stand carriage can proceed along a path which is inclined relative to the horizontal.

14 Claims, 4 Drawing Figures

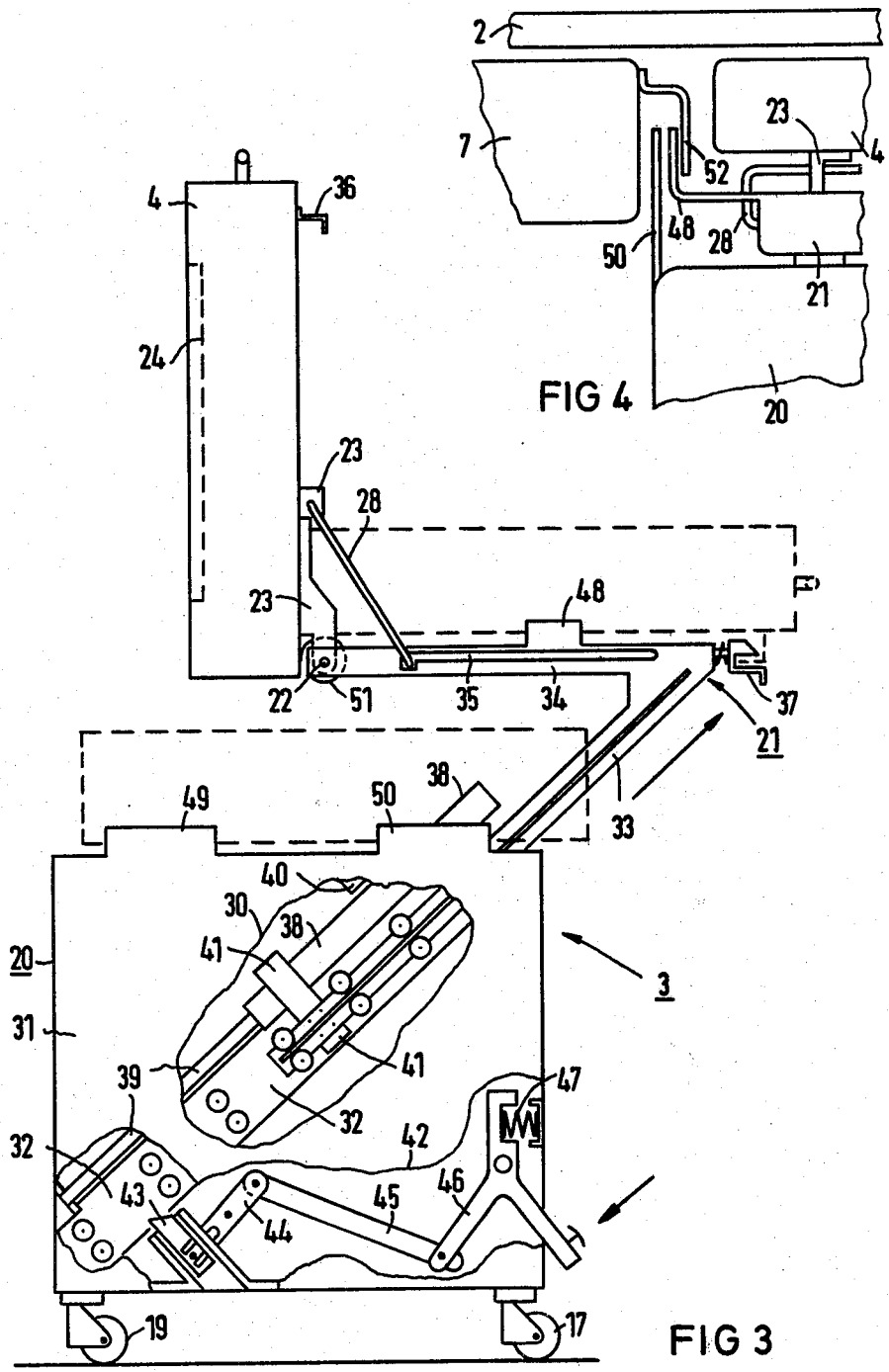

STAND FOR AN X-RAY IMAGE DETECTION APPARATUS WHICH IS INSERTABLE BENEATH THE PATIENT SUPPORT OF AN X-RAY EXAMINATION APPARATUS

BACKGROUND OF THE INVENTION

The invention relates to a stand for an x-ray image detection apparatus which is insertable beneath the patient support platform of an x-ray examination apparatus, comprising a stand carriage which can be driven in a two-dimensional fashion on the floor, a lift carriage which is height-adjustable on the stand carriage, and a support-mounting (which can be pivoted on the lift carriage 90° about a horizontal axis) for mounting the image detection apparatus so that it can be tilted from a position with a horizontal image layer (or film) into a position having a vertical image layer (or film).

The German AS No. 2,557,810 (corresponding to U.S. application Ser. No. 942,667 filed Sept. 15, 1978) discloses a stand for an x-ray image detection apparatus which is comprised of a vertical column or stand which is capable of being moved in a two-dimensional manner on the floor, a lift carriage which is height-adjustable on the vertical column, and two extension arms which are pivotal about a horizontal axis on this lift carriage. At the end of these two extension arms a carrier plate for an image detection apparatus (which is to be threadedly fastened thereto) is pivotally mounted for movement about an additional horizontal axis which is parallel to the first-cited horizontal axis. With this stand, the image detection apparatus, which is fastened on the carrier plate, can be inserted beneath the patient support platform of an x-ray examination apparatus in the case of a lowered lift carriage, lowered extension arms and a horizontally positioned carrier plate, in order, in conjunction with an above-table x-ray tube, to be able to carry out radiographs with vertical ray direction. If one desires to conduct radiographs using the image detection apparatus with a horizontal ray direction, then the stand beneath the patient support platform must be pulled out, the lift carriage on the stand must be pushed up, the two extension arms must be pivoted upwardly by a specified angle, and then the carrier plate with the image detection apparatus must be rotated about its horizontal axis oppositely relative to the extension arms, however, through the same angle. Only then can the stand for the x-ray image detection apparatus again be pushed close to the patient support platform and again be adjusted relative to the x-ray examination apparatus, or the x-ray tube, respectively. Subsequently, the lift carriage must be lowered until the image detection apparatus is positioned directly above the level of the patient support platform. In the case of this construction, the considerable operation outlay is a disturbing factor. In addition, it is a peculiar property of this apparatus that the vertical column, on account of its height, must always be arranged laterally of the patient support platform, and therefore is in the way during the examination of the patient. Also, the constructional outlay which is expended in the case of this stand is considerable.

SUMMARY OF THE INVENTION

The object underlying the invention resides in developing a stand which obstructs the examination of the patient as little as possible and which allows for a simpler handling. In addition, a simpler and more economical construction is to be sought.

In the case of a stand of the type initially cited, therefore, in accordance with the invention, the lift carriage exhibits an essentially angled cross-section with an upwardly extending leg and a horizontal leg; the image detection apparatus, at the free end of the horizontal leg, is pivotally mounted; the stand carriage, the lift carriage (which is guided on the stand carriage and the support-mounting which is pivotally mounted on the lift carriage), are arranged beneath the image detection apparatus, and coupling means capable of being brought into engagement with the x-ray examination apparatus are connected with the stand carriage for the defined positioning of the image detection apparatus relative to the x-ray examination apparatus. This method of construction has as a consequence the fact that the stand, together with the image detection apparatus mounted thereon, in the most frequent type of use, namely during the examination with a vertical path of rays, can be completely driven beneath the patient support platform of the x-ray examination apparatus, and therefore no longer causes any disturbance whatsoever during the examination. In addition, all that this method of construction still requires, during the transition from an examination technique with a vertical path of rays to an examination technique with horizontal path of rays, is a single height adjustment and a single pivot movement. Finally, the coupling means permit a defined and readily reproducible positioning of the image detection apparatus. Time consuming alignments relative to the x-ray examination apparatus, or to the x-ray tube, respectively, are thus not necessary.

An improved adaptation to the working conditions which prevail in the case of x-ray examination apparatus is achieved if the lift carriage, in an expedient embodiment of the invention, is movably guided along a guide track on the stand carriage which is inclined relative to the normal (vertical) direction. If, during the transition from the examination with a vertical ray path to the examination with a horizontal ray path, the lift carriage is obliquely upwardly pushed, then it thereby becomes removed, also in the lateral (horizontal) direction, from the patient support platform. This has as a consequence, the fact that the stand carriage, in the case of a given position of the image detection apparatus above the level of the patient support platform, remains situated more nearly beneath the patient support platform and thus interferes less. Moreover, with this measure, it has become possible for the stand, together with the vertically positioned image detection apparatus, to be able to be inserted further in the direction of the center of the patient support platform, which can be of great advantage, in particular, in the case of examinations of the cranium or of the extremities.

The handling of the stand is substantially facilitated if, in an advantageous further development of the invention, the overall weight of the lift carriage, the support-mounting, and the image detection apparatus is compensated by at least one helper spring mounted along the interior side of a stand wall. In such instances, only minor forces need be exerted in order to carry out the change from the type of operation with a vertical ray path to that with a horizontal ray path.

The handling of the stand can be yet further simplified if, in an expedient further development of the invention, limit stops for the upper and the lower limitation of the lifting path of the lift carriage are provided, which limit stops are matched to the height of the upper supporting surface and of the lower side of the patient support platform. Such limit stops make it possible, during lowering, to bring the lift carriage, at the very first attempt and without any adjustment, into the position in which it is to be inserted beneath the patient support platform with the least possible clearance, or in which, during raising, it is disposed at a desired level above the patient support platform, respectively.

A further simplification of the handling of the stand is achieved if, in an advantageous further development of the invention, guide flanges are arranged at its two longitudinal sides, which flanges are insertable into corresponding profile rails of the x-ray examination apparatus, which profile rails are aligned transversely to the longitudinal axis of the patient support platform. In utilizing a two-dimensionally movable stand carriage, the alignment is thus also maintained when the component of the x-ray examination apparatus, at which coupling is being carried out, is shifted during the examination, such as is the case e.g. with spot film (e.g. film cassette) devices or patient support platforms.

Further details of the invention shall be explained in greater detail on the basis of an exemplary embodiment illustrated in the figures of the accompanying drawing sheets; and other objects, features and advantages will be apparent from this detailed disclosure and from the appended claims.

BRIEF DESCRIPTION OF THE DRAWINGS

FIG. 3 shows an enlarged somewhat diagrammatic lateral view of the stand with portions of a lateral wall broken away to show interior parts; and FIG. 4 is a somewhat diagrammatic partial enlarged frontal view showing parts of the stand in coupling relation with a cooperating profile section of the x-ray examination apparatus at the location indicated by a dot dash circle in FIG. 1.

DETAILED DESCRIPTION

Figure 1:
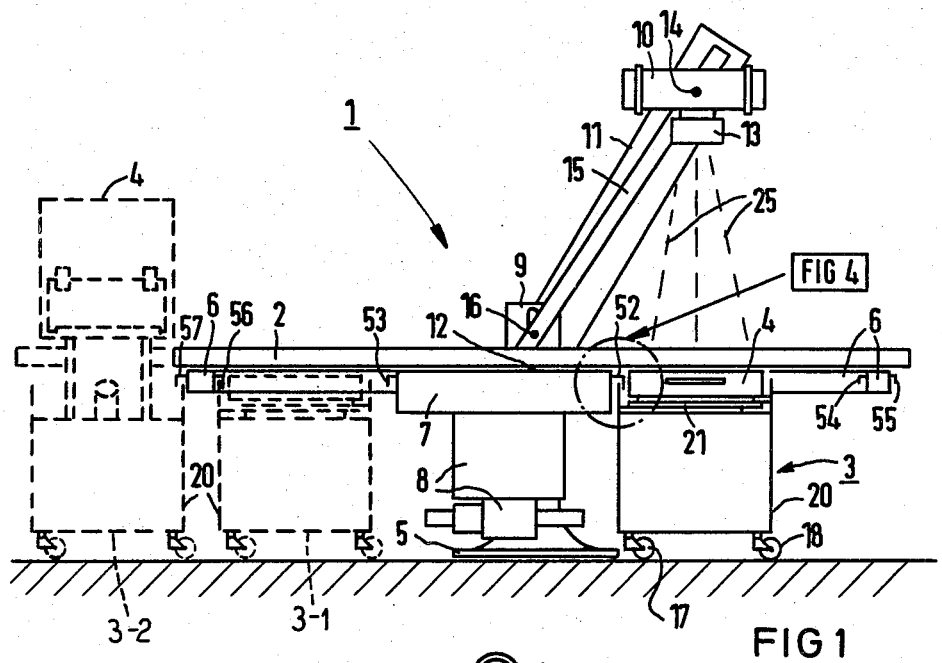
FIG. 1 is a diagrammatic illustration of an x-ray examination apparatus and shows a front view of a stand for an x-ray image detection apparatus, which has been moved into a position beneath the patient support platform.

In FIG. 1, an x-ray examination apparatus 1 can be recognized in which, beneath the horizontally positioned patient support platform 2, a movable stand 3 for an x-ray image detection apparatus 4 is inserted. The x-ray examination apparatus is comprised of a base pedestal 5, resting on the floor, a table frame 6, tiltably mounted about a horizontal axis on the base pedestal 5, in a manner not further illustrated here, on which table frame 6 the patient support platform 2 is mounted in a longitudinally and transversely movable fashion. Beneath the patient support platform 2, a spot film device 7 (e.g. a drawer for receiving film cassettes) with an image intensifier-television installation 8 is mounted on the table frame 6 in a longitudinally displaceable fashion. The base pedestal 5 has a plate-like upright 9 on which an x-ray boom 11 bearing the x-ray tube 10, is pivotally mounted about a horizontal axis 12. The x-ray tube 10, together with the flange mounted depth diaphragm 13, is pivotally mounted about an additional horizontal axis 14 on the x-ray tube boom 11. This last-cited horizontal axis 14 is aligned parallel to the axis 12, about which the tube boom 11 is pivotally mounted on the upright 9. The x-ray tube, if necessary, can be coupled with a laminographic control rod 15, which, in turn, is pivotally mounted about a laminographic axis 16 which is height-adjustable on the upright 9, and which is coupled at its opposite end with the spot film device 7.

Beneath the patient support platform 2, the vertical column or stand 3 for the x-ray image detection apparatus 4 can be recognized as comprising a box-shaped stand carriage 20 which is transportable in a two-dimensional fashion on swivelling rollers such as 17, 18, 19. The stand carriage 20 supports a lifting carriage 21 which is height-adjustably guided and carries a support-mounting 23, FIG. 2, which is pivotal through 90° about a horizontal axis 22. The image detection apparatus 4 is mounted on the support-mounting 23. As shall be later shown on the basis of FIGS. 2 and 3, together with the support-mounting 23, the apparatus 4 can be pivoted from a position with a horizontally aligned image layer (or film) 24 (FIG. 1) into a position with a vertically aligned image layer (or film) 24 (FIG. 3). In FIG. 1, additional operation positions for the stand 3 are indicated in broken lines at 3-1 and 3-2.

Figure 2:
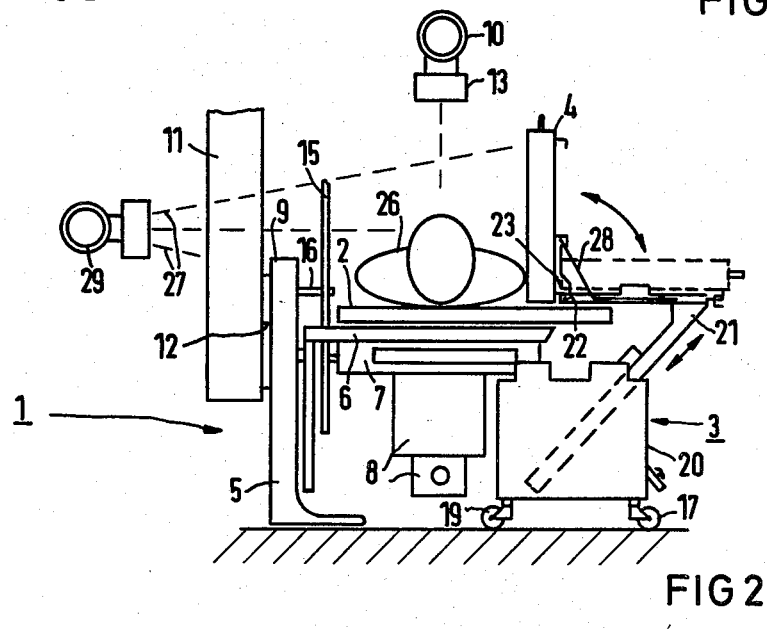
FIG. 2 is a diagrammatic illustration of the x-ray examination apparatus viewed at right angles to FIG. 1 and showing a lateral view of the stand of FIG. 1, the stand being in a different operating mode.

FIG. 2 illustrates the x-ray examination apparatus of FIG. 1 from the side. The image detection apparatus 4, which, in the illustration of FIG. 1, for the purpose of examination with perpendicular x-radiation 25, had been completely driven beneath the patient support platform 2, in FIG. 2, for the purpose of examination of a patient 26 lying on the patient support 2, with horizontal x-radiation 27, is only partially beneath the patient support platform 2. To this end, the lifting carriage 21 of the stand 3 is illustrated extended to an uppermost position. Moreover, the image detection apparatus 4 in FIG. 2 is swung upwardly together with the support-mounting 23 and is locked with a retaining bar 28 on the lifting frame 21. In this position of the image detection apparatus 4, a patient 26, lying on the patient support platform 2, can be examined with horizontally oriented x-radiation 27 with the aid of a second x-ray tube 29 arranged opposite the image detection apparatus 4.

Further details of the construction of the stand 3 for the x-ray image detection apparatus 4 can be recognized from the enlarged illustration of FIG. 3. Through a broken away portion at 30 in the lateral wall 31 of the stand carriage 20, FIG. 3 permits the recognition of one of the two roller tracks 32 (only one illustrated) which are mounted on the inner side of the two mutually opposite sides of the stand carriage 20. The lifting carriage 21, with its lower frame portion 33 consisting of T-sections (only one illustrated) is movable between the latter roller tracks. The roller tracks 32 are so arranged that the lifting carriage 21 can be adjusted in height by movement along a plane which is inclined 45° relative to the horizontal. The frame portion 33 (which is guided in the roller tracks) of the lifting carriage 21 is welded together with a horizontal frame 34. At the upper frontal edge of the horizontal frame 34 of the lifting carriage 21 (which frontal edge is remote from the inclined frame portion 33), the support-mounting 23 which carries the x-ray image detection apparatus 4, is pivotally mounted about the axis 22 aligned parallel to such frontal edge. Accordingly, the x-ray image detection apparatus can be tilted from a horizontal position (indicated in FIG. 3 by broken lines) in which the image layer (or film) is horizontally disposed, into vertical position (illustrated by solid lines in FIG. 3), in which the image layer (or film) is disposed perpendicularly. Thus the pivot axis 22 accommodates a ninety degree angular adjustment of apparatus 4.

The retaining bar 28 is shown in FIG. 3, as locking the x-ray image detection apparatus 4 in its vertical position. The retaining bar 28 is rotatably mounted on the support-mounting 23, and has two free ends which are guided in one groove 35 each (only one illustrated) of the horizontal frame 34 of the lifting carriage 21. In the horizontal position of the x-ray image detection apparatus 4, a profile section 36 engages (or locks) behind a spring-loaded latch 37 carried at a rear edge of the horizontal frame 34 of the lifting carriage 21. A pneumatic spring 38 is mounted on the lower inclined frame portion 33 of the lifting carriage 21, said frame portion being movable along the roller tracks 32 in the stand carriage 20. The piston rod 39 of said pneumatic spring 38 is fixed to the stand carriage 20. At the broken-away portion 30 of the lateral wall 31 of the stand carriage 20, one also recognizes an upper limit stop 40. The latter is engageable with the support-mounting 41 of the pneumatic spring 38 in the uppermost position of the lifting carriage 21. The pneumatic spring 38 is so dimensioned that it somewhat overcompensates the weight of the lifting carriage 21 in addition to the support-mounting 23 and image detection apparatus 4. By means of the pneumatic spring 38 the lifting carriage 21 is therefore pressed against the upper limit stop 40. This limit stop 40 is adjustably designed in a manner not further illustrated here and is matched to the respective height of the patient support platform 2 of the x-ray examination apparatus 1. In the lower region of the roller tracks 32, one recognizes, behind an additional broken-away portion at 42 in the lateral wall 31 of the stand carriage 20, an adjustable limit stop 43 which is capable of being brought into engagement with the support-mounting 41 for the pneumatic spring 38 in the lowest position of the lifting carriage 21. This limit stop 43 is actuated by a foot pedal linkage 46 via a push rod 45 and a centrally pivoted lever 44, which is slotted in bifurcated fashion. The lower limit stop 43 is pressed by a compression spring 47 (acting on linkage 46) so that stop 43 is held in the path of the support-mounting 41 of the pneumatic spring 38.

In FIG. 3, one clearly recognizes one of the guide flanges 48 projecting on both sides of the horizontal frame 34 of the lifting carriage 21. Also on the two lateral walls 31 of the stand carriage 20, two guide flanges 49, 50 in each instance project for the coupling of the image detection apparatus 4 with the x-ray examination apparatus 1. The two guide flanges 49, 50 on each of the two lateral walls of the stand carriage 20 are disposed in the plane of the respective lateral wall 31. The guide flanges 48 (only one visible) on both sides of the horizontal frame 34 of the lifting carriage 21 are guided out laterally to such an extent that they are in alignment with the guide flanges 49, 50 on the lateral walls 31 of the stand carriage 20 and, in the case of a lowered platform, are disposed exactly between the two flanges 49, 50 of the respective lateral wall of the stand carriage. In FIG. 3, the torsion spring 51, looped about the axis 22 can also be recognized by means of which a raising torque is exerted on the image detection apparatus 4 so that the torque due to the weight of the image detection apparatus 4 during raising and lowering is largely compensated.

In the illustration of FIG. 4, which shows a section-enlargement of the coupling location of the stand carriage 20 with the spot film device 7, the guide flanges 48, 49, 50 of the stand carriage and of the lifting carriage 21 appear not quite precisely in alignment; this is only for reasons of clarity. Thus, it is possible, in FIG. 4, to better distinguish the guide flange 48, which projects laterally at the lifting carriage 21, from the guide flanges 49, 50 of the stand carriage 20. FIG. 4 illustrates how the tandem-disposed guide flanges such as 50; 48 of the lateral wall of the stand carriage and of the lifting carriage engage behind an L-shaped profile section 52 on the side of the spot film device 7 of the x-ray examination apparatus 1. Additional profile sections 53, 54, 55, 56, 57, are disposed, as FIG. 1 illustrates, on the other side of the spot film device 7 and on both exterior cross-beams of the table frame 6; namely, on their interior and exterior sides, respectively.

During the examination of a patient 26 lying on the patient support platform 2 of the x-ray examination apparatus 1, the stand 3, with the x-ray image detection apparatus 4, if required, can now be driven-in beneath the patient support platform 2 of the x-ray examination apparatus directly adjacent the spot film device 7 such that the guide flanges 49, 50 of the stand carriage 20 and the guide flanges 48 of the horizontal frame 34 of the lifting carriage 21 engage behind the corresponding L-shaped profile section 52 or 53 of the spot film device 7. In this position, the image layer (or film) 24 is disposed, independently of the pivot position of the x-ray tube boom 11, in a defined distance from the spot film device. This signifies that, in the further course of examination, it is no longer necessary to pay attention to the position of the x-ray image detection apparatus 4, because the latter follows the movements of the spot film device 7 when the latter is entrained by the laminographic rod 15 through pivoting of the x-ray tube boom. Therefore, during the change from an examination operation with the spot film device 7 to radiography operation with the x-ray image detection apparatus 4, proceeding from the position with the perpendicular x-ray tube boom 11, independently of the examination conducted in the meantime, always precisely the same pivot angles of the x-ray tube boom 11 about the horizontal axis 12 and of the x-ray tube 10 about the horizontal axis 14 are required—which pivot angles can be automatically effected by the x-ray examination apparatus—in order to shift the alignment of the x-ray path 25 from the spot film device 7 to the x-ray image detection apparatus 4, and back again. At the same time, in the case of this change of examination mode, the displacement of the patient 26 is less than that in the case of a stationary image detection apparatus 4, because the spot film device 7 with the image detection apparatus 4, during pivoting of the tube boom 11 moves in the direction so as to meet the x-ray tube at the point providing the desired vertically aligned relationship.

Since the guide flanges 49, 50 are applied on both sides of the horizontal frame 34 and of the stand carriage 20, and the profile sections 52 to 57 are applied on both sides of the spot film device 7 and of the table frame 6; namely, on the interior side as well as on the exterior side of the cross-beams, it is possible to couple the stand 3 with the x-ray image detection apparatus at both sides of the spot film device 7, as well as also at both sides of the table frame 6; namely, on the interior side of the table frame as well as on the exterior side of the table frame, as is indicated in FIG. 1 in broken lines (e.g. at 3-1 and 3-2). In these instances, it is guaranteed that the position of the image detection apparatus 4, independently of the shifting of the spot film device 7 during the swivelling of the x-ray tube boom 11, is always positioned relative to the x-ray examination apparatus 1. Particularly in the case of examinations of the cranium, the positions of the stand 3 for the image detection apparatus, which are indicated in FIG. 1 in broken lines at the left at 3-1 and 3-2, are of significance. In this case, the patient support platform 2 can be pushed in a longitudinal direction over or beneath, respectively, the image detection apparatus 4. In all illustrated positions of the image detection apparatus, the stand carriage 20, as a consequence of its minimum overall height, can be driven-in completely beneath the patient support platform 2. It thus in no way obstructs the examination of the patient.

If an examination with a horizontal ray path is to be conducted, it is sufficient to pull out the stand 3 for the image detection apparatus 4 from beneath the patient support platform, to retract the lower limit stop 43 by means of pressure on the foot pedal of linkage 46, via the push rod 45 and the two-arm lever 44, counter to the force of the compression spring 47, in order to give the pneumatic spring 38 the opportunity to press the lifting carriage 21 against the upper limit stop 40. In an upper position of the lifting carriage 21, such as illustrated in FIG. 3, the x-ray image detection apparatus 4 can be tilted, (upon pressing down the spring-loaded latch 37), from its horizontal position, indicated in broken lines, into the vertical position illustrated in fully drawn lines, and said x-ray image detection apparatus 4 can be locked in vertical position by means of engagement of the retaining bar 28. In this position, the image detection apparatus 4, as is illustrated in FIG. 2, through driving-in of the stand carriage 20 beneath the patient support platform 2, can be pushed as far as may be desired over the patient support platform 2. Any type of adjustment measures for the height or the pivot angle of the image detection apparatus are not necessary here. As a consequence of the inclined arrangement of the frame section 33, which is movably mounted between the roller tracks 32, said frame section 33 virtually provides no obstruction to the insertion.

Instead of the utilization of a pneumatic spring 38, also other types of springs or also counterweights can be employed. It would also be possible to secure the rollers to the lifting carriage and to allow them to run between guides which are fixedly secured on the lateral walls of the stand carriage 20. Finally, it is also conceivable to mount the lifting carriage 21 such that it is horizontally movable in the stand carriage 20 and to guide the support-mounting on the lifting carriage 21 such that it is perpendicularly displaceable (or movable). This construction, however, would have the disadvantage that an additional adjustment movement would be necessary during the transition from the examination with vertical ray path to an examination with horizontal ray path. In this instance, also, for the previously cited reasons, each of the adjustment movements could be limited by limit stops.

It will be apparent that many modifications and variations may be effected without departing from the scope of the novel concepts and teachings of the present invention.

I claim as my invention:

1. A stand for an x-ray image detection apparatus which is insertable beneath a patient support platform of an x-ray examination apparatus, said stand comprising: a stand carriage (20) which can be transported on the floor in a two-dimensional fashion, a lifting carriage (21) which is height-adjustable on the stand carriage, said lifting carriage comprising a support-mounting (23) which is pivotal through 90° about a horizontal axis on the lifting carriage, and image detection apparatus (4) fastened to said support-mounting (23) so as to be tiltable from a position with a horizontal image plane into a position with a vertical image plane, wherein the improvement comprises: said lifting carriage (21) having an essentially angled configuration including a horizontal leg (34) having a free end carrying said support mounting (23) so that the image detection apparatus (4) is pivotally mounted at the free end of the horizontal leg (34); the stand carriage (20), the lifting carriage (21) and the support-mounting (23) being arranged so as to be beneath the image detection apparatus (4); and coupling means (48, 49, 50) connected with the stand carriage (20) and capable of being brought into engagement with an x-ray examination apparatus for the defined positioning of the image detection apparatus (4) relative to an x-ray examination apparatus (1).

2. A stand according to claim 1, with said lifting carriage being mounted so as to be horizontally displaceably in the stand carriage and the support-mounting being height-adjustably mounted on the lifting carriage.

3. A stand according to claim 1, with spring means (38) in the stand carriage (20) for compensating the overall weight of the lifting carriage (21), the support-mounting (23) and the image detection apparatus (4).

4. A stand according to claim 1, with limit stops (40, 43) on the stand matched to the height of a support surface and to a lower side of a patient support platform (2), and providing for the upper and the lower limitation of the path of movement of the lifting carriage (21).

5. A stand according to claim 1, with guide flanges (48, 49, 50) are arranged on two opposite sides of the stand carriage (20) and the lifting carriage (21) which guide flanges are capable of insertion in corresponding profile sections (52 to 57) of an x-ray examination apparatus (1), which profile sections extend transversely to a longitudinal axis of a patient support platform (2).

6. A stand according to claim 1, with coupling means (49, 50) on the stand carriage (20) for coupling with an under-table spot film device (7) of an x-ray examination apparatus (1).

7. A stand according to claim 1, with at least one spring (51) compensating the torque associated with the support-mounting (23) during its pivotal movement in effecting tilting of the image detection apparatus (4).

8. A stand according to claim 1, with limit stop means (28, 35, 36, 37, 40, 41, 43) for defining a position of the image detection apparatus (4) with a horizontal image plane and for defining a position of said image detection apparatus with a vertical image plane.

9. A stand according to claim 1, with spring means (38) in the stand carriage (20) for compensating the overall weight of the lifting carriage (21), the support-mounting (23) and the image detection apparatus (4), said spring means (38) somewhat overcompensating the overall weight of the lifting carriage (21) and the image detection apparatus (4), and latch means (43) for holding the lifting carriage (21) in its lowest position against the lifting action of said spring means.

10. A stand according to claim 1, with coupling means (49, 50) on the stand carriage (20) for coupling to a table frame (6) of an x-ray examination apparatus (1).

11. A stand according to claim 10, with said coupling means (49, 50) being engageable at a front side of a table frame (6) of an x-ray examination apparatus (1).

12. A stand according to claim 1, with the stand carriage (20) having guide means (32) inclined relative to the perpendicular, and the lifting carriage (21) being displaceably guided on the stand carriage (20) along the guide means (32).

13. A stand according to claim 12, with said guide means (32) for the lifting carriage (21) being inclined at an angle in the range from approximately 20° to approximately 70° relative to the perpendicular.

14. An x-ray examination apparatus comprising a patient support platform (2) and coupling elements (52, 53, 54, 55, 56, 57) having operative association with said platform (2), and a stand (3) insertable beneath said patient support platform, said stand (3) comprising a stand carriage (20) which can be transported on the floor in a two-dimensional fashion, a lifting carriage (21) which is height-adjustable on the stand carriage, said lifting carriage comprising a support-mounting (23) which is pivotal through 90° about a horizontal axis on the lifting carriage, and image detection apparatus (4) fastened to said support-mounting (23) so as to be tiltable from a position with a horizontal image plane into a position with a vertical image plane, said lifting carriage (21) carrying said support-mounting (23) so that the image detection apparatus (4) is pivotally mounted relative to said lifting carriage (21); the stand carriage (20), the lifting carriage (21) and the support-mounting (23) being arranged so as to be beneath the image detection apparatus (4); and coupling means (48, 49, 50) connected with the stand carriage (20) and capable of being brought into engagement with said coupling elements (52, 53, 54, 55, 56, 57) for facilitating the defined positioning of the image detection apparatus (4) relative to the patient support platform (2).

* * * * *